United States Patent
Tian et al.

(10) Patent No.: US 7,761,178 B2
(45) Date of Patent: Jul. 20, 2010

(54) AUTOMATED PROCESS CONTROL USING AN OPTICAL METROLOGY SYSTEM OPTIMIZED WITH DESIGN GOALS

(75) Inventors: Xinkang Tian, San Jose, CA (US); Manuel Madriaga, San Jose, CA (US); Ching-Ling Meng, Sunnyvale, CA (US); Mihail Mihaylov, San Jose, CA (US)

(73) Assignee: Tokyo Electron Limited, Tokyo (JP)

( * ) Notice: Subject to any disclaimer, the term of this patent is extended or adjusted under 35 U.S.C. 154(b) by 273 days.

(21) Appl. No.: 12/141,892

(22) Filed: Jun. 18, 2008

(65) Prior Publication Data

US 2009/0319075 A1    Dec. 24, 2009

(51) Int. Cl.
*G06F 19/00* (2006.01)
*G01N 21/00* (2006.01)

(52) U.S. Cl. .................. 700/97; 700/98; 700/121; 356/237.4; 356/237.5; 702/81; 702/82; 716/1; 716/19

(58) Field of Classification Search ........... 700/97–98, 700/109, 119–121; 356/625, 636, 237.4–237.5; 702/81–82, 117, 155–159, 166–167; 716/1, 716/4, 19–21
See application file for complete search history.

(56) References Cited

U.S. PATENT DOCUMENTS

| | | | | |
|---|---|---|---|---|
| 5,347,356 A * | 9/1994 | Ota et al. | ................... | 356/490 |
| 5,468,580 A * | 11/1995 | Tanaka | ..................... | 430/22 |
| 5,926,690 A * | 7/1999 | Toprac et al. | ................ | 438/17 |
| 6,304,999 B1 * | 10/2001 | Toprac et al. | ................ | 716/4 |
| 6,451,621 B1 * | 9/2002 | Rangarajan et al. | .......... | 438/14 |
| 6,609,086 B1 * | 8/2003 | Bao et al. | ................... | 702/189 |
| 6,701,206 B1 * | 3/2004 | Markle et al. | ............... | 700/121 |
| 6,778,273 B2 | 8/2004 | Norton et al. | | |
| 6,785,638 B2 | 8/2004 | Niu et al. | | |
| 6,891,626 B2 | 5/2005 | Niu et al. | | |
| 6,943,900 B2 | 9/2005 | Jakatdar et al. | | |
| 7,280,229 B2 * | 10/2007 | Li et al. | ..................... | 356/625 |
| 7,444,196 B2 * | 10/2008 | Scheer et al. | ............... | 700/109 |
| 2005/0192914 A1 * | 9/2005 | Drege et al. | ................... | 706/12 |
| 2005/0209816 A1 * | 9/2005 | Vuong et al. | ................ | 702/167 |
| 2005/0251771 A1 * | 11/2005 | Robles | ......................... | 716/5 |
| 2009/0063077 A1 * | 3/2009 | Liu et al. | ..................... | 702/82 |

OTHER PUBLICATIONS

U.S. Appl. No. 12/050,053, filed Mar. 17, 2008 for Tian et al.

(Continued)

*Primary Examiner*—Ramesh B Patel
(74) *Attorney, Agent, or Firm*—Manuel B. Madriaga

(57) ABSTRACT

Provided is a method of designing an optical metrology system for measuring structures on a workpiece wherein the optical metrology system is configured to meet a plurality of design goals. The design of the optical metrology system is optimized by using collected design goal data in comparison to the set plurality of design goals. In one embodiment, the optical metrology system is used for stand alone metrology systems. In another embodiment, the optical metrology system is integrated with a fabrication cluster in semiconductor manufacturing. At least one parameter determined from a diffraction signal measured using the optical metrology system is transmitted to the fabrication cluster. The at least one parameter is used to modify at least one process variable or equipment setting of the fabrication cluster.

23 Claims, 9 Drawing Sheets

OTHER PUBLICATIONS

U.S. Appl. No. 12/050,919, filed Mar. 18, 2008 for Tian et al.
U.S. Appl. No. 12/057,316, filed Mar. 27, 2008 for Tian et al.
U.S. Appl. No. 12/057,332, filed Mar. 27, 2008 for Tian et al.
U.S. Appl. No. 12/057,346, filed Mar. 27, 2008 for Tian et al.
U.S. Appl. No. 12/059,610, filed Mar. 31, 2008 for Meng et al.
U.S. Appl. No. 12/141,754, filed Jun. 18, 2008 for Tian et al.
U.S. Appl. No. 12/141,867, filed Jun. 18, 2008 for Tian et al.

* cited by examiner

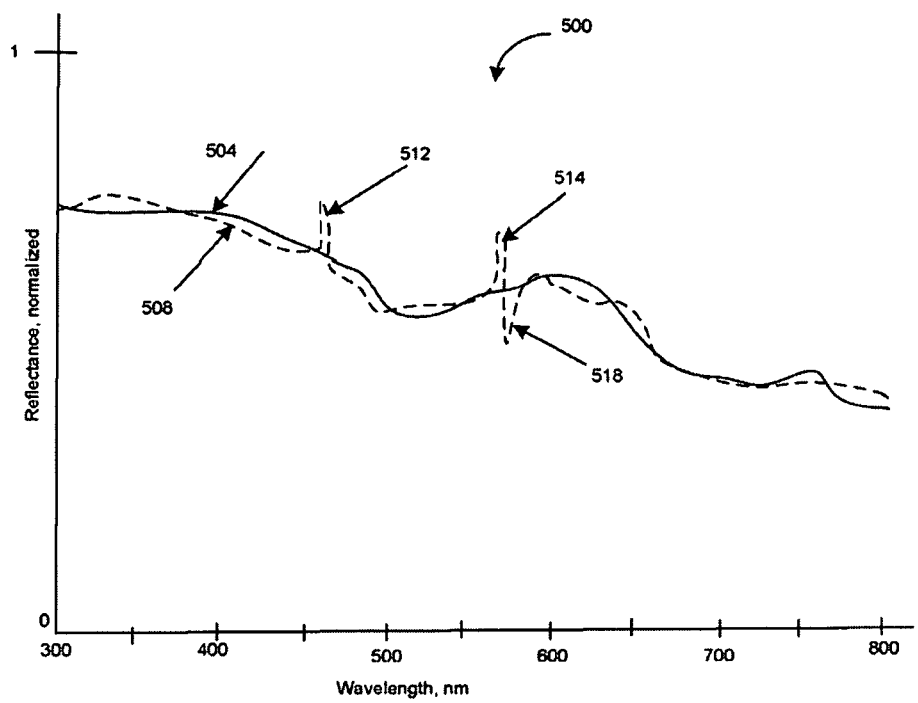
FIG. 5
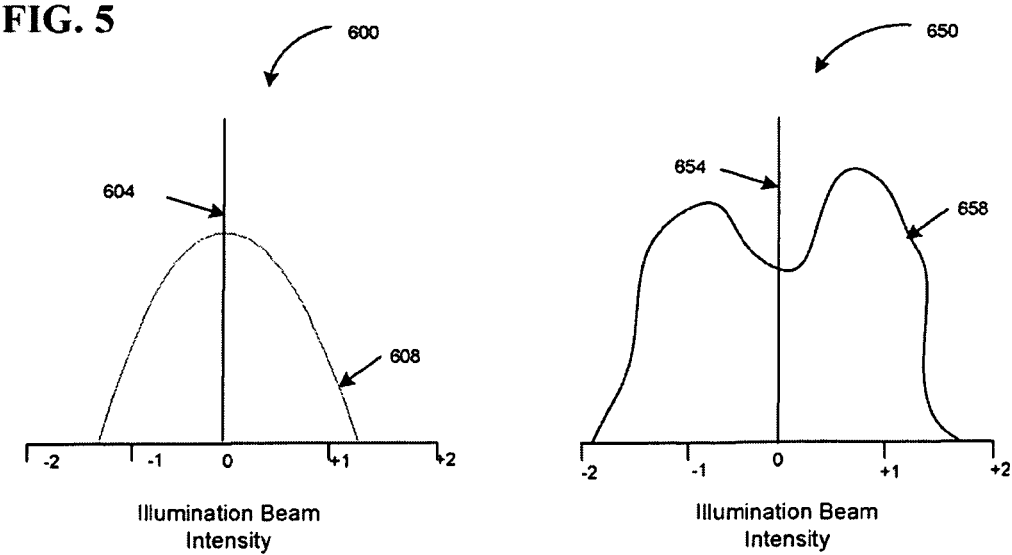
FIG. 6A  FIG. 6B

AUTOMATED PROCESS CONTROL USING AN OPTICAL METROLOGY SYSTEM OPTIMIZED WITH DESIGN GOALS

BACKGROUND

1. Field

The present application generally relates to the design of an optical metrology system to measure a structure formed on a workpiece, and, more particularly, to a method and an apparatus for process control using an optical metrology system optimized to meet a plurality of design goals.

2. Related Art

Optical metrology involves directing an incident beam at a structure on a workpiece, measuring the resulting diffraction signal, and analyzing the measured diffraction signal to determine various characteristics of the structure. The workpiece can be a wafer, a substrate, photomask or a magnetic medium. In manufacturing of the workpieces, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional system, the diffraction signal collected from illuminating the periodic grating (the measured diffraction signal) is compared to a library of simulated diffraction signals. Each simulated diffraction signal in the library is associated with a hypothetical profile. When a match is made between the measured diffraction signal and one of the simulated diffraction signals in the library, the hypothetical profile associated with the simulated diffraction signal is presumed to represent the actual profile of the periodic grating. The hypothetical profiles, which are used to generate the simulated diffraction signals, are generated based on a profile model that characterizes the structure to be examined. Thus, in order to accurately determine the profile of the structure using optical metrology, a profile model that accurately characterizes the structure should be used.

With increased requirement for throughput, decreasing size of the test structures, smaller spot sizes, and lower cost of ownership, there is greater need to optimize design of optical metrology systems to meet several design goals. Characteristics of the optical metrology system including throughput, range of measurement capabilities, accuracy and repeatability of diffraction signal measurements are essential to meeting the increased requirement for smaller spot size and lower cost of ownership of the optical metrology system.

SUMMARY

Provided is a method of designing an optical metrology system for measuring structures on a workpiece where the optical metrology system is configured to meet a plurality of design goals. The design of the optical metrology system is optimized by using collected design goal data in comparison to the set plurality of design goals. In one embodiment, the optical metrology system is used for standalone metrology systems. In another embodiment, the optical metrology system is integrated with a fabrication cluster in semiconductor manufacturing. At least one parameter determined from a signal measured using the optical metrology system is transmitted to the fabrication cluster. The at least one parameter is used to modify at least one process variable or equipment setting of the fabrication cluster.

BRIEF DESCRIPTION OF DRAWINGS

FIG. 5 depicts a graph of a reflectance as a function of wavelength for a simulated diffraction signal and a measured diffraction signal.

FIG. 6A depicts a graph of an illumination beam intensity as a function of distance from the center of a uniform beam whereas FIG. 6B depicts a graph of an illumination beam intensity from the center of an asymmetrical non-uniform beam.

DETAILED DESCRIPTION

In order to facilitate the description of the present invention, a semiconductor wafer may be utilized to illustrate an application of the concept. The systems and processes equally apply to other workpieces that have repeating structures. The workpiece may be a wafer, a substrate, disk, or the like. Furthermore, in this application, the term structure when it is not qualified refers to a patterned structure.

Figure 1A:
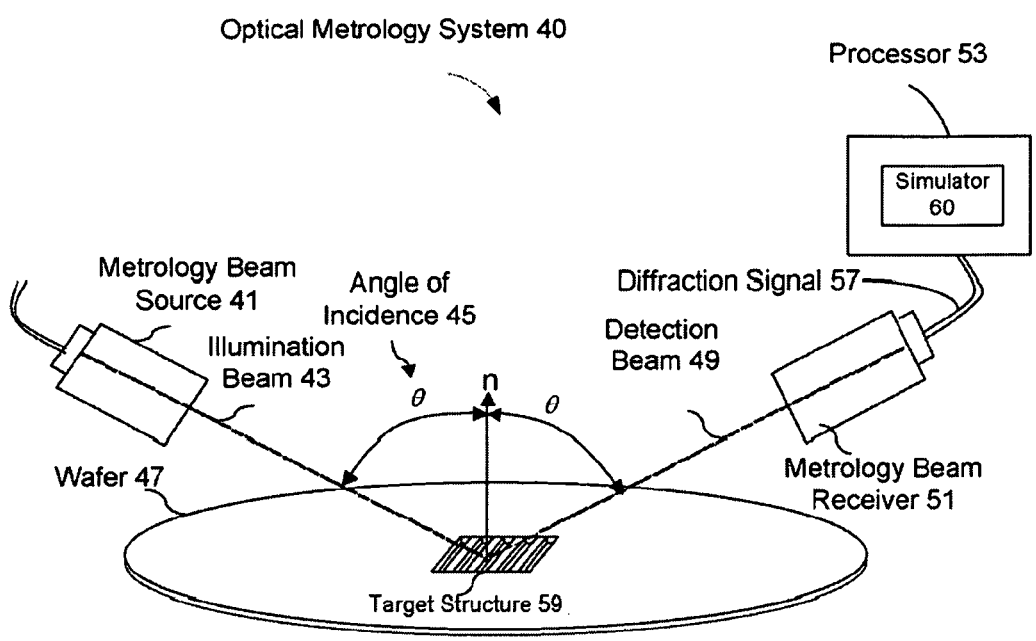
FIG. 1A is an architectural diagram illustrating an exemplary embodiment where an optical metrology system can be utilized to determine the profiles of structures formed on a semiconductor wafer.

FIG. 1A is an architectural diagram illustrating an exemplary embodiment where optical metrology can be utilized to determine the profiles or shapes of structures fabricated on a semiconductor wafer. The optical metrology system 40 includes a metrology beam source 41 projecting a metrology illumination beam 43 at the target structure 59 of a wafer 47. The metrology beam 43 is projected at an incidence angle θ (label 45 in FIG. 1A) towards the target structure 59. The diffracted detection beam 49 is measured by a metrology beam receiver 51. A measured diffraction signal 57 is transmitted to a processor 53. The processor 53 compares the measured diffraction signal 57 against a simulator 60 of simulated diffraction signals and associated hypothetical profiles representing varying combinations of critical dimensions of the target structure and resolution. The simulator can be either a library that consists of a machine learning system, pre-generated data base and the like (e.g., this is a library system), or on demand diffraction signal generator that solves the Maxwell equation for a giving profile (e.g., this is a regression system). In one exemplary embodiment, the diffraction signal generated by the simulator 60 instance best matching the measured diffraction signal 57 is selected. The hypothetical profile and associated critical dimensions of the selected simulator 60 instance are assumed to correspond to the actual cross-sectional shape and critical dimensions of the features of the target structure 59. The optical metrology system 40 may utilize a reflectometer, an ellipsometer, or other optical metrology device to measure the diffraction beam or signal. An optical metrology system is described in U.S. Pat. No. 6,913,900, entitled "GENERATION OF A LIBRARY OF PERIODIC GRATING DIFFRACTION SIGNAL", issued on Sep. 13, 2005, which is incorporated herein by reference in its entirety.

Simulated diffraction signals can be generated by applying Maxwell's equations and using a numerical analysis technique to solve Maxwell's equations. It should be noted that various numerical analysis techniques, including variations of rigorous coupled-wave analysis (RCWA), can be used. For a more detail description of RCWA, see U.S. Pat. No. 6,891,626, entitled "CACHING OF INTRA-LAYER CALCULATIONS FOR RAPID RIGOROUS COUPLED-WAVE ANALYSES", filed on Jan. 25, 2001, issued May 10, 2005, which is incorporated herein by reference in its entirety.

Simulated diffraction signals can also be generated using a machine learning system (MLS). Prior to generating the simulated diffraction signals, the MLS is trained using known input and output data. In one exemplary embodiment, simulated diffraction signals can be generated using an MLS employing a machine learning algorithm, such as back-propagation, radial basis function, support vector, kernel regression, and the like. For a more detailed description of machine learning systems and algorithms, see U.S. patent application Ser. No. 10/608,300, entitled "OPTICAL METROLOGY OF STRUCTURES FORMED ON SEMI-CONDUCTOR WAFERS USING MACHINE LEARNING SYSTEMS", filed on Jun. 27, 2003, which is incorporated herein by reference in its entirety.

Figure 1B:
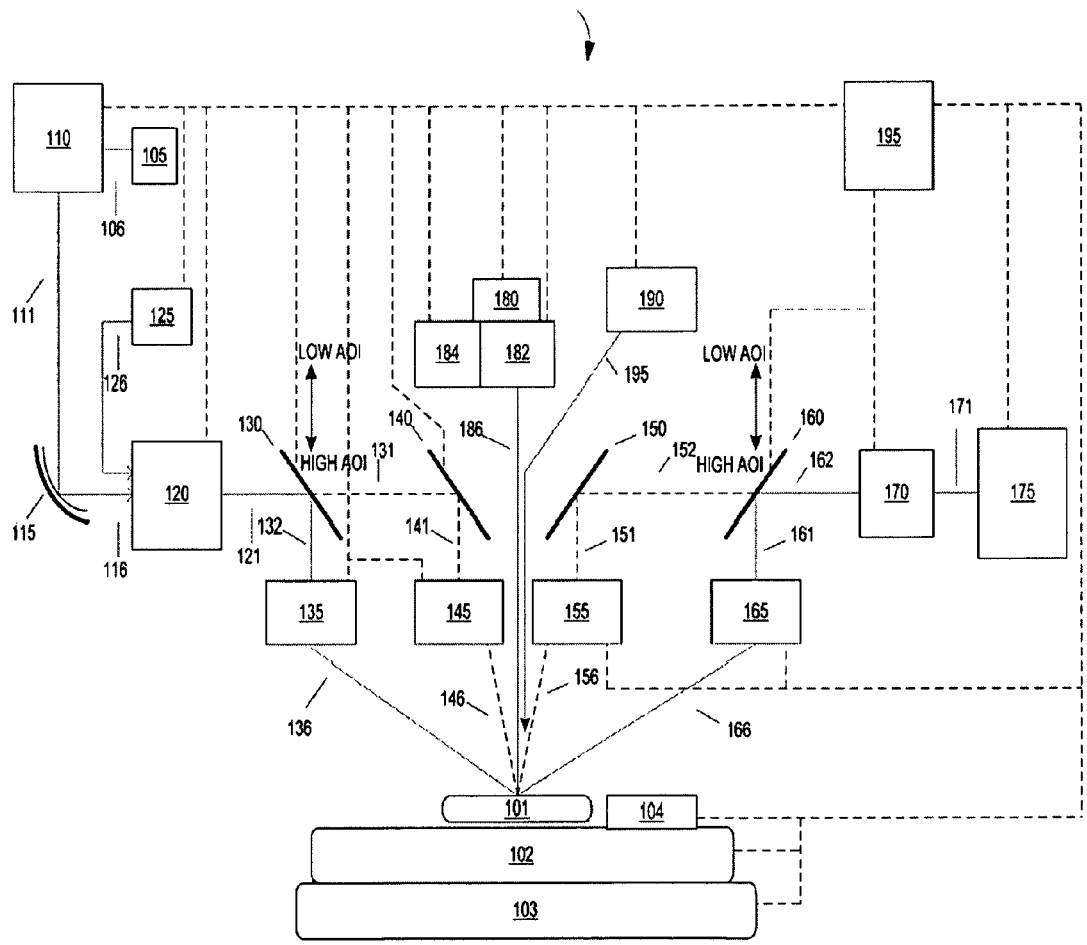
FIG. 1B depicts an exemplary optical metrology system in accordance with embodiments of the invention.

FIG. 1B shows an exemplary block diagram of an optical metrology system in accordance with embodiments of the invention. In the illustrated embodiment, an optical metrology system 100 can comprise a lamp subsystem 105, and at least two optical outputs 106 from the lamp subsystem can be transmitted to an illuminator subsystem 110. At least two optical outputs 111 from the illuminator subsystem 110 can be transmitted to a selector subsystem 115. The selector subsystem 115 can send at least two signals 116 to a beam generator subsystem 120. In addition, a reference subsystem 125 can be used to provide at least two reference outputs 126 to the beam generator subsystem 120. The wafer 101 is positioned using an X-Y-Z-theta stage 102 where the wafer 101 is adjacent to a wafer alignment sensor 104, supported by a platform base 103.

The optical metrology system 100 can comprise a first selectable reflection subsystem 130 that can be used to direct at least two outputs 121 from the beam generator subsystem 120 on a first path 131 when operating in a first mode "LOW AOI" (AOI, Angle of Incidence) or on a second path 132 when operating in a second mode "HIGH AOI". When the first selectable reflection subsystem 130 is operating in the first mode "LOW AOI", at least two of the outputs 121 from the beam generator subsystem 120 can be directed to a first reflection subsystem 140 as outputs 131, and at least two outputs 141 from the first reflection subsystem can be directed to a high angle focusing subsystem 145, When the first selectable reflection subsystem 130 is operating in the second mode "HIGH AOI", at least two of the outputs 121 from the beam generator subsystem 120 can be directed to a low angle focusing subsystem 135 as outputs 132. Alternatively, other modes in addition to "LOW AOI" and "HIGH AOI" may be used and other configurations may be used.

When the metrology system 100 is operating in the first mode "LOW AOI", at least two of the outputs 146 from the high angle focusing subsystem 145 can be directed to the wafer 101. For example, a high angle of incidence can be used. When the metrology system 100 is operating in the second mode "HIGH AOI", at least two of the outputs 136 from the low angle focusing subsystem 135 can be directed to the wafer 101. For example, a low angle of incidence can be used. Alternatively, other modes may be used and other configurations may be used. The optical metrology system 100 can comprise a high angle collection subsystem 155, a low angle collection subsystem 165, a second reflection subsystem 150, and a second selectable reflection subsystem 160.

When the metrology system 100 is operating in the first mode "LOW AOI", at least two of the outputs 156 from the wafer 101 can be directed to the high angle collection subsystem 155. For example, a high angle of incidence can be used. In addition, the high angle collection subsystem 155 can process the outputs 156 obtained from the wafer 101 and high angle collection subsystem 155 can provide outputs 151 to the second reflection subsystem 150, and the second reflection subsystem 150 can provide outputs 152 to the second selectable reflection subsystem 160. When the second selectable reflection subsystem 160 is operating in the first mode "LOW AOI" the outputs 152 from the second reflection subsystem 150 can be directed to the analyzer subsystem 170. For example, at least two blocking elements can be moved allowing the outputs 152 from the second reflection subsystem 150 to pass through the second selectable reflection subsystem 160 with a minimum amount of loss.

When the metrology system 100 is operating in the second mode "HIGH AOI", at least two of the outputs 166 from the wafer 101 can be directed to the low angle collection subsystem 165. For example, a low angle of incidence can be used. In addition, the low angle collection subsystem 165 can process the outputs 166 obtained from the wafer 101 and low angle collection subsystem 165 can provide outputs 161 to the second selectable reflection subsystem 160. When the second selectable reflection subsystem 160 is operating in the second mode "HIGH AOI" the outputs 162 from the second selectable reflection subsystem 160 can be directed to the analyzer subsystem 170.

When the metrology system 100 is operating in the first mode "LOW AOI", high incident angle data from the wafer 101 can be analyzed using the analyzer subsystem 170, and when the metrology system 100 is operating in the second mode "HIGH AOI", low incident angle data from the wafer 101 can be analyzed using the analyzer subsystem 170.

Metrology system 100 can include at least two measurement subsystems 175. At least two of the measurement subsystems 175 can include at least two detectors such as spectrometers. For example, the spectrometers can operate from the Deep-Ultra-Violet to the visible regions of the spectrum.

The metrology system 100 can include at least two camera subsystems 180, at least two illumination and imaging subsystems 182 coupled to at least two of the camera subsystems 180. In addition, the metrology system 100 can also include at least two illuminator subsystems 184 that can be coupled to at least two of the imaging subsystems 182.

In some embodiments, the metrology system 100 can include at least two auto-focusing subsystems 190. Alternatively, other focusing techniques may be used.

At least two of the controllers (not shown) in at least two of the subsystems (105, 110, 115, 120, 125, 130, 135, 140, 145, 150, 155, 160, 165, 170, 175, 180, 182, 190, and 195) can be used when performing measurements of the structures. A controller can receive real-signal data to update subsystem, processing element, process, recipe, profile, image, pattern, and/or model data. At least two of the subsystems (105, 110, 115, 120, 125, 130, 135, 140, 145, 150, 155, 160, 165, 170, 175, 180, 182, and 190) can exchange data using at least two Semiconductor Equipment Communications Standard (SECS) messages, can read and/or remove information, can feed forward, and/or can feedback the information, and/or can send information as a SECS message.

Those skilled in the art will recognize that at least two of the subsystems (105, 110, 115, 120, 125, 130, 135, 140, 145, 150, 155, 160, 165, 170, 175, 180, 182, 190, and 195) can include computers and memory components (not shown) as required. For example, the memory components (not shown) can be used for storing information and instructions to be executed by computers (not shown) and may be used for storing temporary variables or other intermediate information during the execution of instructions by the various computers/processors in the metrology system 100. At least two of the subsystems (105, 110, 115, 120, 125, 130, 135, 140, 145, 150, 155, 160, 165, 170, 175, 180, 185, and 190) can include the means for reading data and/or instructions from a computer readable medium and can comprise the means for writing data and/or instructions to a computer readable medium. The metrology system 100 can perform a portion of or all of the processing steps of the invention in response to the computers/processors in the processing system executing at least two sequences of at least two instructions contained in a memory and/or received in a message. Such instructions may be received from another computer, a computer readable medium, or a network connection. In addition, at least two of the subsystems (105, 110, 115, 120, 125, 130, 135, 140, 145, 150, 155, 160, 165, 170, 175, 180, 182, and 190) can comprise control applications, Graphical User Interface (GUI) components, and/or database components.

It should be noted that the beam when the metrology system 100 is operating in the first mode "LOW AOI" with a high incident angle data from the wafer 101 all the way to the measurement subsystems 175, (output 166, 161, 162, and 171) and when the metrology system 100 is operating in the second mode "HIGH AOI" with a low incident angle data from the wafer 101 all the way to the measurement subsystems 175, (output 156, 151, 152, 162, and 171) is referred to as diffraction signal(s).

Figure 2:
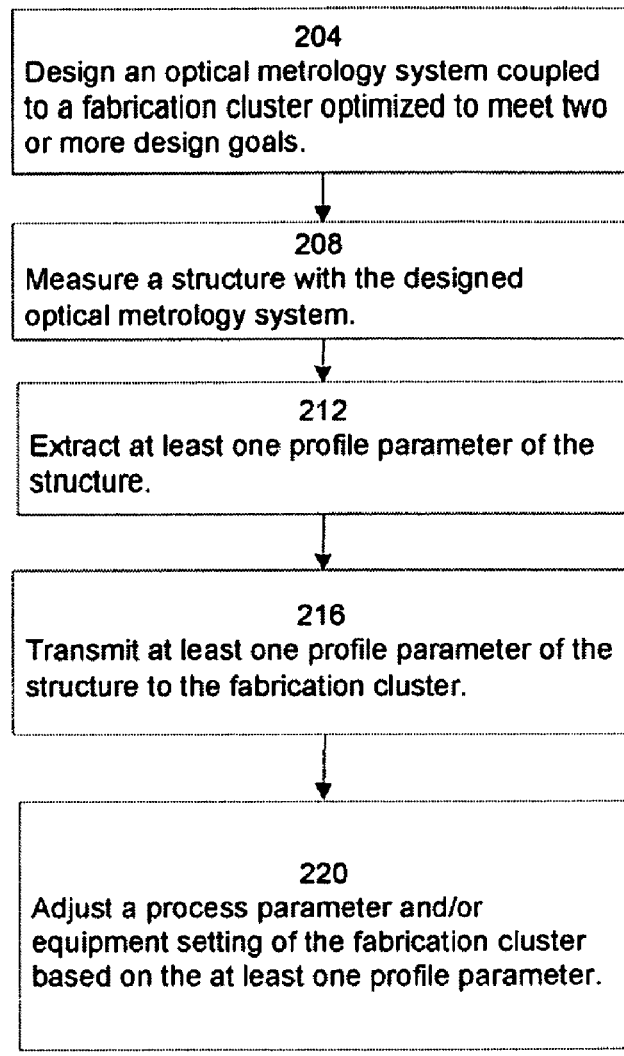
FIG. 2 depicts an exemplary flowchart for designing a metrology system for extracting structure profile parameters and controlling a fabrication process.

FIG. 2 depicts an exemplary flowchart for designing an optical metrology system for extracting structure profile parameters and controlling a fabrication process for semiconductors (or integrated circuits, or electronic devices). In this exemplary embodiment, the optical metrology system is integrated in a fabrication cluster. It is understood that the optical metrology system may be in a standalone metrology system with or without automated equipment delivering and retrieving work pieces from the optical metrology system. In step 204, an optical metrology system coupled to a fabrication cluster is designed to meet two or more design goals. The fabrication cluster may be a lithography, etch, cleaning, chemical-mechanical polishing fabrication cluster, deposition cluster, or the like. The optical metrology system includes an optical metrology tool such as a spectroscopic reflectometer, spectroscopic ellipsometer, hybrid optical device, and the like. The detail steps for designing the optical metrology system are included in the description associated with the flowchart in FIG. 4.

Referring to FIG. 2, the two or more design goals may include: accuracy of the measured diffraction signals assessed by comparing the profile parameter determined from the measured diffraction signal to the profile parameter determined using a reference tool such as scanning electron microscope (SEM); repeatability of the measured diffraction signals, either static or dynamic repeatability or both, typically measured as statistical variation from mean; range of spot sizes of illumination beam that can be measured by the optical metrology system; range of sizes of the measurement spot; throughput in the number of workpieces measured per unit time; and types and range of applications measured. Types and range of applications measured may include line and space or other one dimensional repeating structures, complex transistor structures, two dimensional repeating structures such as vias, contact holes, posts, and trenches, structures with surface, edge, or shape roughness, irregularly shaped structures such as structures having peanut-shaped islands, conical structures, structures with convex or concave surfaces, structures in multiple layers such as overlay and chemical-mechanical polishing (CMP) applications, and other complex structures such as double patterning structures, multiple pitch structures or iso-dense structures. In alternate embodiments, design goals may also include tool-to-tool matching ranges to a similar tool or to a reference tool or to a fleet of tools, reliability of the optical metrology system expressed as up time or mean time between failures, time needed to develop libraries for extracting profile parameters or time needed to train machine learning systems for extracting profile parameters, or cost of ownership measured in dollars needed for service, repair cost, and maintenance costs, and the like. In one embodiment, the optical metrology system may either be integrated in a process tool such as an etcher or be part of a stand alone metrology module.

Still referring to FIG. 2, in step 208, a structure is measured with the designed optical metrology system generating a diffraction signal. As mentioned above, the workpiece may be a wafer, a substrate, disk, photomask or the like. In step 212, at least one profile parameter of the structure is extracted from the measured diffraction signal using one or more systems, such as the regression system, the library system or the machine learning system described above. In step 216, at least one extracted profile parameter of the structure is transmitted to the fabrication cluster. Extracted profile parameters may include critical dimensions such as bottom width, top width or sidewall angle of the structure. In other embodiments, extracted profile parameters may include any profile parameter of the structure. In step 220, at least one process parameter or equipment setting of the fabrication cluster is adjusted based on the at least one transmitted profile parameters.

Figure 3:
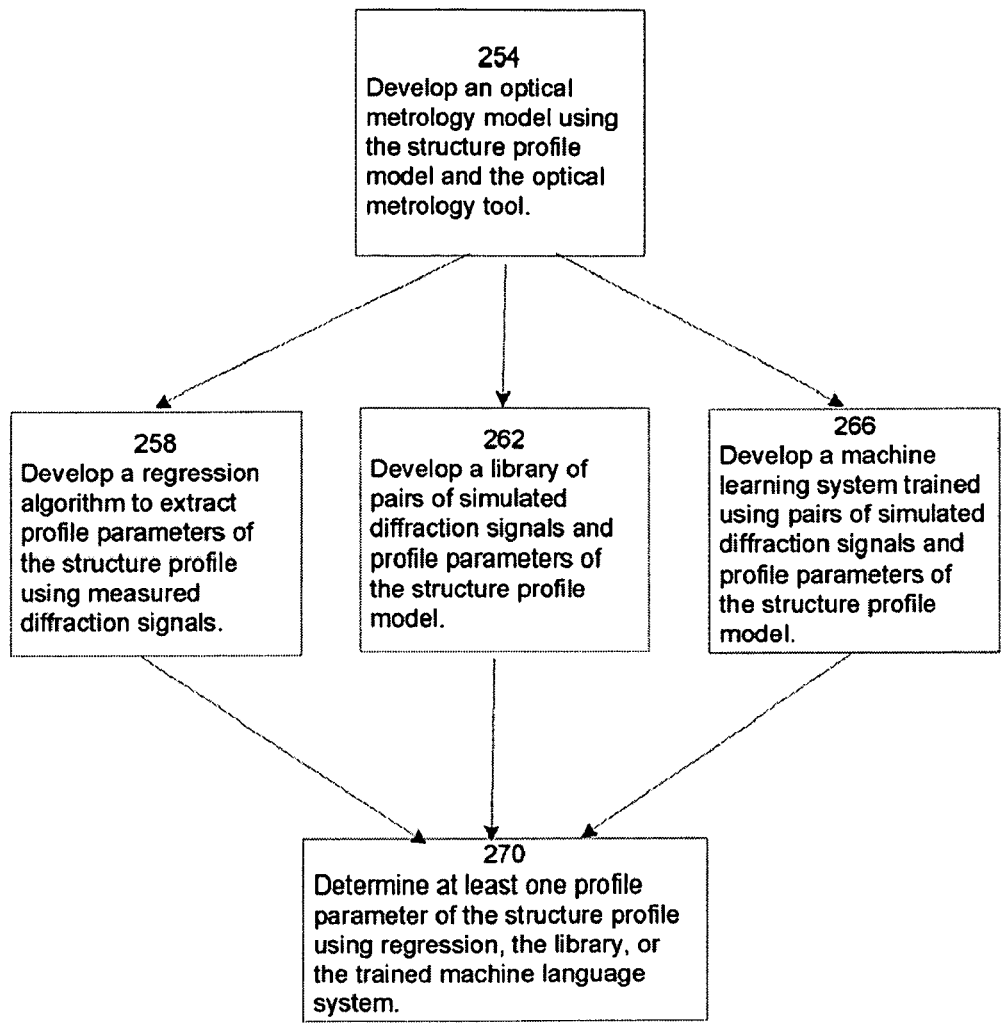
FIG. 3 depicts an exemplary flowchart for a system for extracting structure profile parameters using measurements from the optical metrology system.

FIG. 3 depicts an exemplary flowchart for a system for extracting profile parameters using measurements from the optical metrology system. In step 254, an optical metrology model is developed using the profile model of the structure and the designed optical metrology system. As mentioned above, the profile of the structure may be a simple line and space grating or a more complex group of repeating structures such as posts, contact holes, vias, or combinations of different shapes structures in a repeating pattern of unit cells. For a detailed description of modeling two-dimensional repeating structures, refer to U.S. patent application Ser. No. 11/061,303, entitled "OPTICAL METROLOGY OPTIMIZATION FOR REPETITIVE STRUCTURES", by Vuong, et al., filed on Apr. 27, 2004, and is incorporated in its entirety herein by reference. The optical metrology model includes characterization of the illumination beam that is used to illuminate the structure and characterization of the detection beam diffracted from the structure.

In step 258, a regression algorithm is developed to extract the profile parameters of the structure profile using measured diffraction signals. Typically, the regression algorithm compares a series of simulated diffraction signals generated from a set of profile parameters where the simulated diffraction signal is matched to the measured diffraction signal until the matching criteria are met. For a more detailed description of a regression-based process, see U.S. Pat. No. 6,785,638, entitled "SYSTEM AND SYSTEM FOR DYNAMIC LEARNING THROUGH A REGRESSION-BASED LIBRARY GENERATION PROCESS", filed on Aug. 6, 2001, which is incorporated herein by reference in its entirety.

In step 262, a library of pairs of simulated diffraction signals and profile parameters of the structure are developed. For a more detailed description of an exemplary library-based process, see U.S. Pat. No. 6,943,900, entitled "GENERATION OF A LIBRARY OF PERIODIC GRATING DIFFRACTION SIGNALS", issued on Sep. 13, 2005, which is incorporated herein by reference in its entirety. In step 266, an MLS trained using pairs of simulated diffraction signals and profile parameters are developed. The trained MLS is configured to generate a set of profile parameters as output based on an input measured diffraction signal. For a more detailed description of a generating and using a trained MLS, see U.S. Pat. No. 7,280,229, entitled "EXAMINING A STRUCTURE FORMED ON A SEMICONDUCTOR WAFER USING MACHINE LEARNING SYSTEMS", filed on Dec. 3, 2004, which is incorporated herein by reference in its entirety. In step 270, at least one profile parameter of the structure profile is determined using the regression algorithm, the library, and/or the trained MLS. It should be noted that the steps described above, (254, 258, 262, 264, 268, and 270), apply to an optical metrology system in a fabrication cluster or to a standalone optical metrology system.

Figure 4:
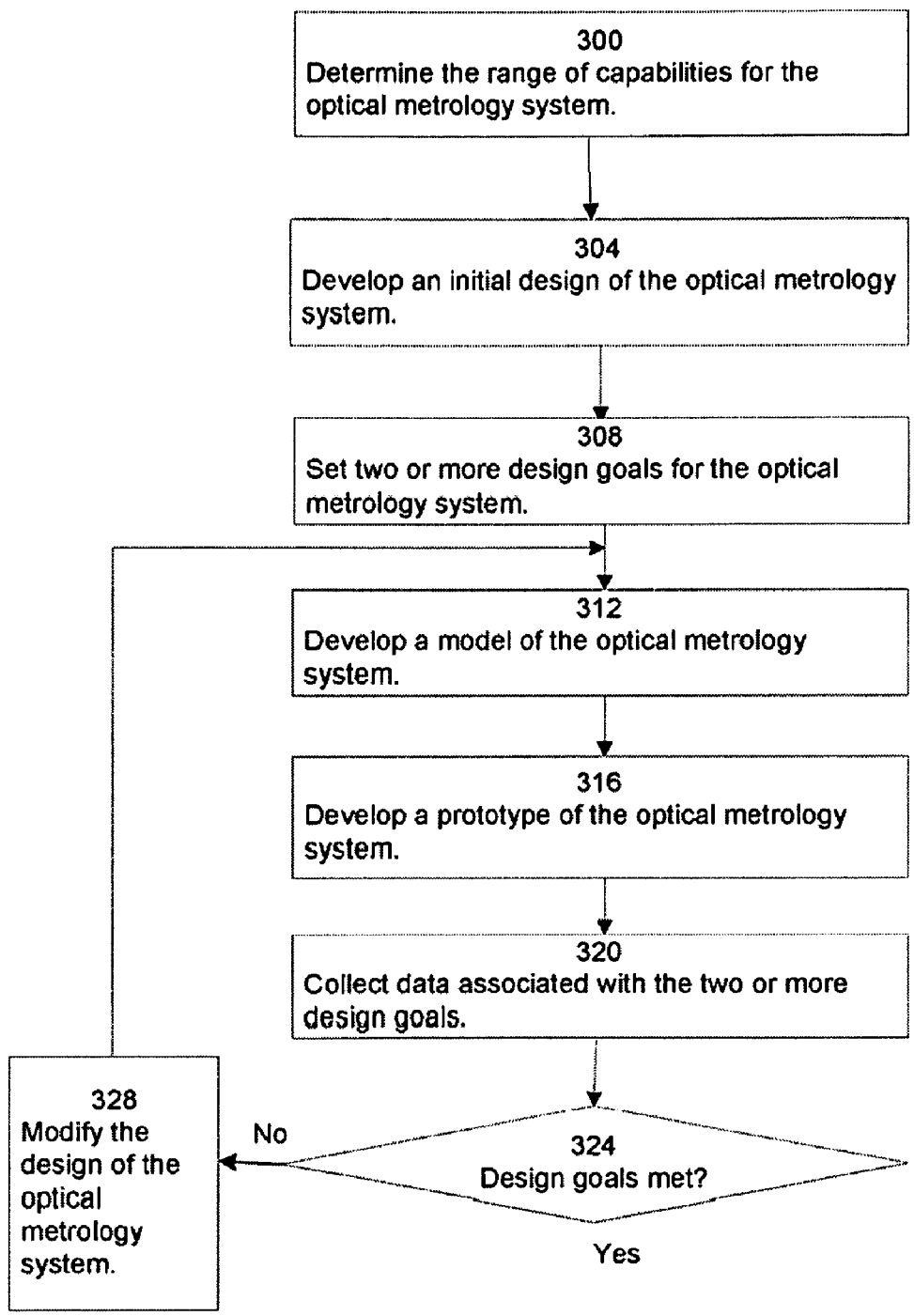
FIG. 4 depicts an exemplary flowchart for optimizing the design of an optical metrology system based on a plurality of design goals.

FIG. 4 depicts an exemplary flowchart for optimizing the design of an optical metrology system based on achieving two or more design goals. In step 300, the range of capabilities of the optical metrology system is determined. The range of capabilities of the optical metrology system may include the types of workpieces or in the case of semiconductor workpieces, wafer applications that can be measured which in turn determines the number and type of measurement beams and optical paths, the range of illumination angles of incidence, number of measurement sites per wafer, the number of measurements per site, and the like. For example, if an optical metrology system is designed to measure one-dimensional repeating structures comprising lines and spaces, two measurement beams may be specified and the illumination beam of incidence would more likely use a fixed angle of incidence. If an optical metrology system is designed to measure both one-dimensional repeating structures and complex two-dimensional repeating structures, two or more measurement beams with a range of illumination beam angles of incidence may be specified. Furthermore, the range of capabilities determined for the optical metrology system may require different types of illumination devices, types of beam focusing optics, types of polarization of the beams, types of collection beam equipment, detectors, and processors.

In step 304, an initial design of the optical metrology system is developed based on the range of capabilities determined in the step 300. The initial design includes components of the optical metrology system comprising light sources, a homogenizer to produce a uniform light spot, focusing optics for the illumination beams and coating specification for the focusing optics, polarizers for the illumination beams and detection beams, a motion control system for moving the workpiece during pattern recognition and diffraction signal measurement, collecting optics for the detection beams, at least two detectors for measuring the diffraction signals and efficiency of the detector gratings, use of a nitrogen-purged system, a first processor for converting the measured diffraction output to diffraction data, data storage for storing profile parameter extraction algorithms, libraries, or trained machine learning systems, and a second processor for extracting at least one parameter of the structure from the diffraction signal. Furthermore, the measured diffraction signal may be processed to increase the signal to noise ratio by using the first processor and algorithms for minimizing systematic noise from the signal.

Referring to FIG. 4, in step 308, two or more design goals for optical metrology system are set. As mentioned above, the design goals can include accuracy of the measured diffraction signals compared to a reference tool such as a SEM, an AFM (atomic force microscope) and the like. Accuracy may also be measured in comparison to a previously calibrated scatterometry tool. Another design goal is repeatability of the measured diffraction signals, either static or dynamic repeatability or both, typically measured as statistical variation from the mean. Another design goal is the range of spot sizes of illumination beam that can be measured by the optical metrology system as well as the range of sizes of the measurement spot. The optical metrology system may be designed to be able to measure a spot size of 32 by 32 micron or smaller. The throughput in the number of workpieces measured per unit time is another design goal. The throughput can be number of workpieces measured per unit time, such as an hour. As mentioned above, the optical metrology system may either be integrated in a process tool such as an etcher or be part of a stand alone metrology module. Another design goal is the type of applications that can be measured by the optical metrology system. As mentioned above, types of applications measured may include one dimensional repeating structures, complex transistors structures, two dimensional repeating structures, structures with surface, edge, or shape roughness, irregular shapes such as peanut shaped islands, convex or concave surfaces, multiple layers structures such as overlay and structures prior to chemical-mechanical polishing, complex structures such double patterning structures, multiple pitch structures or iso-dense structures. Further design goals may also include tool-to-tool matching ranges to a similar tool or to a reference tool or to a fleet of tools, reliability of the optical metrology system expressed as up time or mean time between failures, time needed to develop libraries for extracting profile parameters or time needed to train machine learning systems for extracting profile parameters, or cost of ownership measured in dollars needed for service, repair cost, and maintenance costs, and the like.

In step 312, a metrology model for the optical metrology system is developed. The metrology model includes components of the optical metrology system that have a functional association with set two or more design goals. Assume the two or more design goals include a throughput rate of at least 200 wafers per hour and an accuracy of structure measurement of 3 nanometers (nm) or less compared to cross-section SEM. For the throughput rate, the metrology model can include components associated with the time budget of measuring a wafer for a given application, the number of measurement sites, the number of measurements per site, speed of moving the wafer or the measurement optics to the site, alignment of the site, focusing of the beam, collection of the diffraction signal, processing of the diffraction signal, extraction of profile parameters such critical dimension (CD), sidewall angle, or width of the structure. For a detailed discussion of an optical metrology model designed to optimize an operating time budget, refer to U.S. patent application Ser. No. 12/050,053, entitled "METHOD OF DESIGNING AN OPTICAL METROLOGY SYSTEM OPTIMIZED FOR OPERATING TIME BUDGET", by Tian, et al., filed on Mar. 18, 2008 and is incorporated in its entirety herein by reference.

Referring to FIG. 4, step 312, the metrology model for the example will also include components of the optical metrology system that have a functional association with the accuracy of the measurement as expressed in the difference between the profile parameter extracted using the measured diffraction signal and one measured using a cross-section SEM, where the difference is 3 nm or less. One operating characteristic of the optical metrology system that is correlated with accuracy of the measurement includes intensity of the illumination and detection beams from the one or more light sources up to and including the detection subsystem. Another operating characteristic of the optical metrology system that is correlated to accuracy of the measurement includes signal to noise ratio (SNR) of the illumination signal, the detection signal or both. The SNR is affected by the type of optical components used and the environment in which the optical components operate in, such as the use of an optical environment purged with nitrogen gas, use of a homogenizer to provide highly uniform illumination, use of temperature control subsystems to keep the temperature of the light sources within a narrow temperature range, use of a motion control system that minimizes vibrations of the chuck and workpiece, and the like. In other embodiments, the SNR may also be enhanced using software algorithms to reduce the noise in the measured diffraction signal. Use of algorithms to reduce the noise in the measured diffraction signal are described in U.S. patent application Ser. No. 12/018,028, entitled "NOISE-REDUCTION METROLOGY MODELS", by Li, et al., filed on Jan. 22, 2008 and U.S. patent application Ser. No. 11/371,752, entitled "WEIGHTING FUNCTION TO ENHANCE MEASURED DIFFRACTION SIGNALS IN OPTICAL METROLOGY", by Vuong, et al., filed on Mar. 8, 2006, and are incorporated in their entirety herein by reference.

In step 316 of FIG. 4, a prototype of the optical metrology model is developed. The prototype may include two or more of the metrology components coupled so as to simulate the actual connections and settings in the actual devices in production. For example, the prototype may comprise the light sources and optical components up to and including the focusing optics in the illumination optical path. In another embodiment, the prototype may comprise the light sources, focusing optical components, polarizers, and other optics in the illumination optical path, collection optical components, polarizers, and other optics in the detection optical path. In still another embodiment, the prototype may comprise all optical components from the light sources all the way to the detectors. In still another embodiment, the prototype may include a fully assembled optical metrology system.

In step 320, the data associated with the two or more design goals are collected. For example, assume the two or more design goals include a throughput rate of at least 200 wafers per hour and an accuracy of 3 nanometers (nm) or less compared to cross-section SEM measurements. As mentioned above, the data collected to determine the throughput rate comprises the total time budget needed to complete the measurement of all the sites for the wafer. Time budget applies to metrology steps that cannot be overlapped with other steps in the metrology cycle and the total time budget for each wafer is converted to the equivalent throughput rate, such as wafers per hour. For a detailed discussion of an optical metrology model designed to optimize an operating time budget, refer to U.S. patent application Ser. No. 12/050,053, entitled "METHOD OF DESIGNING AN OPTICAL METROLOGY SYSTEM OPTIMIZED FOR OPERATING TIME BUDGET", by Tian, et al., filed on Mar. 18, 2008, and is incorporated in its entirety herein by reference. Also, as mentioned above, accuracy of measurement in comparison to a reference metrology tool is a function of the intensity of the light sources, illumination beams, and detection beams. Accuracy is also affected by the signal to noise ratio of the metrology beams. For a detailed discussion of an optical metrology system optimized using operating criteria such as signal intensity and signal to noise ratio, refer to U.S. patent application Ser. No. 12/057,316, entitled "DESIGNING AN OPTICAL METROLOGY SYSTEM OPTIMIZED WITH SIGNAL CRITERIA", by Tian, et al., filed on Mar. 27, 2008 and is incorporated in its entirety herein by reference.

In step 324, collected design goal data are compared to the set two or more design goals. If the set two or more design goals are not met, in step 328, the design of the optical metrology system is modified and steps 312, 316, 320, 324, and 328 are iterated until the two or more design goals are met. In step 328, modification of the design of the optical metrology system depends on the set two or more design goals. As in the example above, the two or more design goals include measurement of a spot size of 32 by 32 microns or less and a repeatability of measurements with a 3-sigma variance of 2 nanometers or less. For the spot size design goal, modification of the design can include changing the numerical aperture of a set of optical components by substituting different optics and/or using a different optics vendor. Other modifications of the design can include changing the aperture to allow more or less light or changing the shape of the aperture. Other embodiments include design modifications that includes use of apodizers, changing the light source to use different kinds of bulbs, changing the light source or using a different light source from a different vendor, using different size of lenses, changing the aperture shape, changing the angle of incidence of the illumination beam closer to normal or vice versa, using a combination of large aperture optics and a small aperture slit, and the like. For the repeatability design goal, modification of the design can include the same design changes to increase the SNR mentioned above. In addition, design modifications can include keeping the light source in a narrow range of temperature, increasing the accuracy of the auto focus subsystem, increasing the precision of the polarizer rotating mechanism, reducing the electronic noise in the detection system, increasing the loading and positioning accuracy of the workpiece loading mechanism, increasing the wafer alignment accuracy, and the like.

Other design modifications can include selecting two or more light sources utilizing different ranges of wavelengths instead of utilizing one light source, illuminating the structure at substantially the same spot with the two or more beams from the two or more light sources at the same time, measuring the two or more diffraction signals off the structure and using one or more detectors for each of the two or more diffraction signals; selecting an off-axis reflectometer wherein the angle of incidence of the illumination beam is substantially around 28 degrees instead of a normal or near normal angle of incidence; selecting an off-axis reflectometer wherein the angle of incidence of the illumination beam is substantially around 65 degrees instead of a near normal reflectometer or instead of 28 degrees; or reducing the number of optical components needed to implement the design.

Still referring to step 328, modification of the design of the of the optical metrology system can also include using a selectable angle of incidence for the illumination beam to optimize accuracy of the diffraction measurement instead of a fixed angle of incidence of the illumination beams, higher efficiency grating and higher efficiency signal detector, configurable numerical aperture for the focusing optics, light source, and the like. In other embodiments, modification of the design of the of the optical metrology system can include selecting a first polarizer in the illumination path and a second polarizer (or analyzer) in the detection path, wherein the first and second polarizers are configured to increase the signal to noise ratio of the illumination and detection beams respectively instead of regular polarizers or substituting the first polarizer and the second polarizer with polarizers from another vendor, replacing mirrors and focusing optics with different quality coatings, replacement of diffractive optic with reflective optics, and the like.

In one embodiment mentioned above, one of the two or more design goals may be used to qualify the accuracy of the measurement by comparing to a reference measurement such as an AFM or a cross-section SEM measurement. Modification of the design can include minimizing the effect of system noise and artifacts in the measurement process. Referring to FIG. 5, a reflectance graph 500 is depicted as a function of wavelength. In the reflectance graph 500, a simulated reflectance signal 504 and a measured diffraction signal 508 are provided. The simulated reflectance signal 504 is based on a model of the optical metrology system, the model including a profile model of the structure on the workpiece and the model of the optical metrology tool. Simulation of the reflectance signal is performed, for example, using a numerical analysis solution of the Maxwell equations on electromagnetic diffraction such as RCWA. The measured diffraction signal 508 tracks the simulated reflectance signal 504 except for artifacts 512, 514, and 518. The artifacts 512, 514, and 518 may be due to a variety of causes such as polarizer leakage due to additional or residual polarization or polarization caused by imperfections or contamination of the structure surface, scattering of the detection beam due to surface roughness of the structure, misalignment of an optical component, and the like. Modifications of the design of the optical metrology system may include replacement of the polarizer, calibration of optical components to minimize the effect of deviations in the specified tolerance and/or imperfections of the components during manufacture, or changes to the structure model to incorporate the surface roughness of the structure.

Still referring to FIG. 5, another cause for artifacts of the measured diffraction signal can be due to lack of symmetry or uniformity in the intensity of the illumination beam. Referring to FIG. 6A, the graphical illustration 600 of the illumination beam intensity as a function of the distance from a center 604 of the illumination beam. An intensity graph 608 is substantially a Gaussian distribution where the intensity of the illumination beam diminishes from the center 604 of the beam. Referring to FIG. 6B, a graphical illustration 650 of the illumination beam intensity as a function of the distance from a center 654 of the illumination beam shows irregularity of an intensity graph 658 where the intensity of the illumination beam dips in around the center 654 of the illumination beam. If the illumination beam included in the optical metrology tool model assumed a symmetrical and uniform intensity beam, the design change to increase accuracy of measurements may include changing the model to incorporate the unevenness of the illumination intensity, doing additional calibration of the light sources and optical components to minimize the residual effects of misalignment, imperfections during manufacture, and/or contamination during handling, or replacing the light source or using a different light source model or another light source vendor, or using a beam homogenizer.

Figure 7:
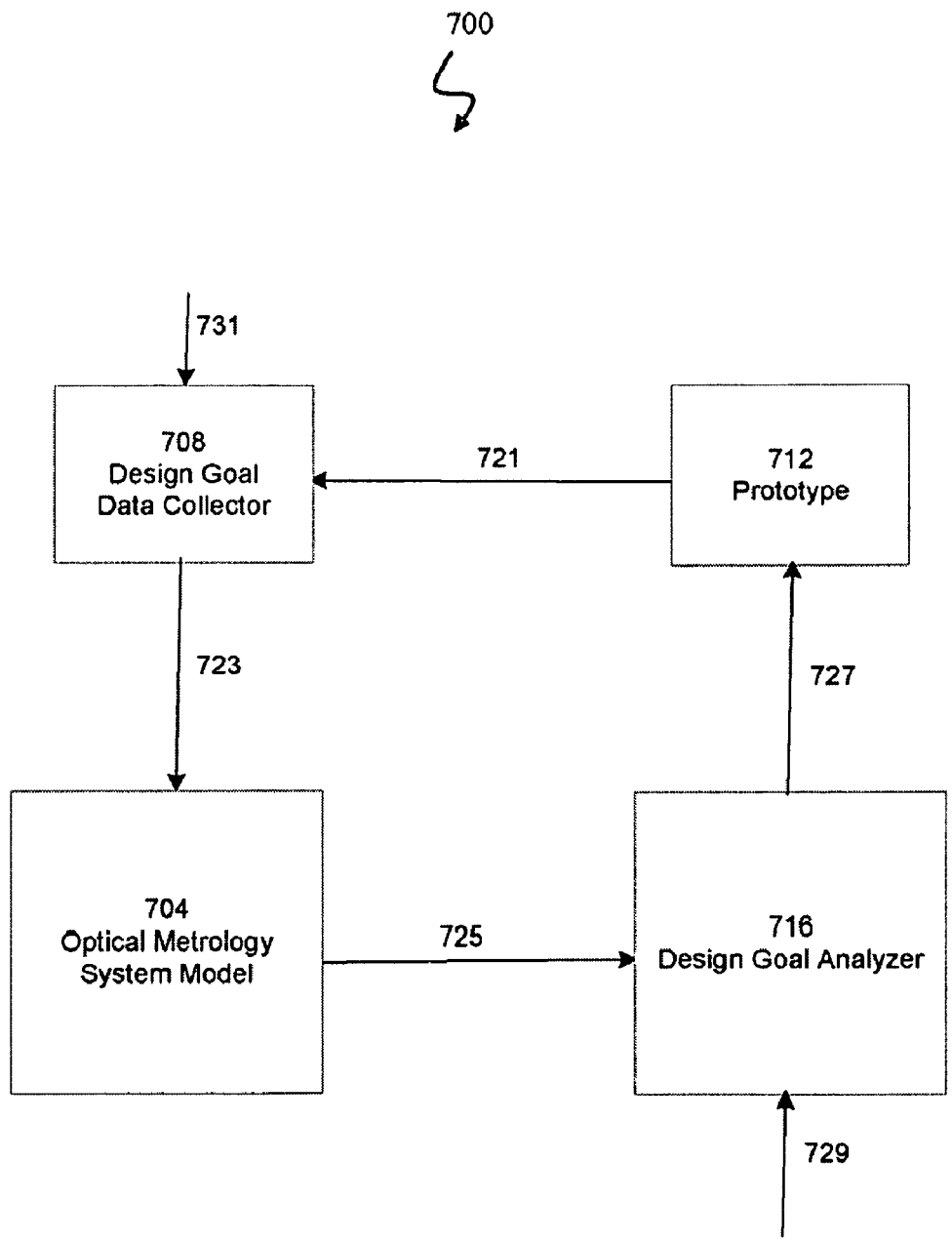
FIG. 7 is an exemplary block diagram of a system to optimize the design of an optical metrology system using a plurality of design goals.

FIG. 7 is an exemplary block diagram of a system 700 to optimize the design of the optical metrology system to meet two or more design goals. The system 700 comprising an optical metrology system model 704, a design goal data collector 708, a prototype 712, and a design goal analyzer 716 are coupled to collect and optimize the optical metrology system of a particular design based on the set of two or more design goals. The optical metrology system model 704 is based on an initial design of the optical metrology system. The initial design is driven by the range of capabilities of the optical metrology system. As mentioned above, the range of capabilities includes types of applications measured and may include one dimensional repeating structures, complex transistors structures, two dimensional repeating structures, and complex structures such double patterning structures, multiple pitch structures or iso-dense structures. Included in the optical system model 704 are components of the optical metrology system that arc functionally associated with the two or more design goals. The prototype 712 comprises optical metrology system components that are configured to simulate the performance of the actual optical metrology system. The prototype 712 for an optical metrology system, two or more of the actual metrology components are utilized to test out the optical path and connections between mechanical and electronic components. For example, the prototype may include a motion control subsystem (not shown) programmed to position the wafer to the selected measurement sites, focusing subsystems in the illumination and detection optical paths, and a pattern recognition subsystem (not shown) to determine the orientation of the wafer, where the pattern recognition subsystem is coupled to the motion control subsystem.

Referring to FIG. 7, design goal data 721, for example, signal intensity or SNR at different points in the optical path measured in the prototype 712 are transmitted to the design goal data collector 708. In addition, design goal data from the vendors or historical design goal data 731 for similar optical components are input into the design goal data collector 708, and collections of design goal data 723 are further sent to the optical metrology system model 704. The collections of design goal data 723 are processed by the optical metrology system model 704 to generate design goal data for each design goal 725 and are transmitted to the design goal analyzer 716. The design goal analyzer 716 compares the two or more design goals collected and assembled from all the sources to corresponding input two or more design goals 729. Based on the results of the comparison in the design goal analyzer 716, modifications to the optical metrology system design 727 are determined and transmitted to and implemented in the prototype 712.

As mentioned above, modification of the design of the optical metrology system depends on the set two or more design goals. As in the example above, assume the two or more design goals include measurement of a spot size of 32 by 32 microns or less and a repeatability of measurements with a 3-sigma variance of 2 nanometers or less. For the spot size design goal, modification of the design can include changing the numerical aperture of a set of optical components by substituting different optics, and/or using a different optics vendor. Other modifications of the design can include changing the slit to allow more or less light or changing the shape of the slit. Other embodiments include design modifications including use of apodizers, changing the light source to use different kinds of bulbs, changing the light source or using a different light source from a different vendor, using different size of lenses, changing the angle of incidence of the illumination beam closer to normal or vice versa, using a combination of large aperture optics and a small aperture slit, and the like. For the repeatability design goal, modification of the design can include the same design changes to increase the SNR mentioned above. In addition, design modifications can include keeping the light source in a narrow range of temperature, increasing the accuracy of the auto focus subsystem, increasing the precision of the polarizer rotating mechanism, reducing the electronic noise in the detection system, increasing the loading and positioning accuracy of the workpiece loading mechanism, increasing the wafer alignment accuracy, and the like. Other modification of the design of the optical metrology system can also include using a selectable angle of incidence for the illumination beam to optimize accuracy of the diffraction measurement instead of a fixed angle of incidence of the illumination beams; higher efficiency grating and higher efficiency signal detector, configurable numerical aperture for the focusing optics, light source, and the like.

In the other embodiment mentioned above, one of the two or more design goals may be accuracy of the measurement compared to a reference measurement such as an AFM or a cross-section SEM. Modification of the design can include changing the model of the optical metrology tool included in the optical metrology system model 704. Steps to increase accuracy can include minimizing the effect of system noise and artifacts in the measurement process discussed in connection with FIG. 5. Also, as mentioned above, modifications of the design of the optical metrology system may include replacement of the polarizer, calibration of optical components to minimize the effect of deviations in the specified tolerance and/or imperfections of the components during manufacture.

Referring to FIG. 7, the changes to the design of the prototype 712 are also incorporated in the design goal data collector 708 and into the optical metrology system model 704. The set of design goal data 721 from the prototype 712 and from vendor data 731 are input into the design goal data collector 708 and transmitted to the optical metrology system model 704, generating new design goal data to compare to the set two or more design goals. Changes to the design of the prototype 712, updates to the design goal data collector 708 and to the optical metrology system model 704, and processing in the design goal analyzer 716 are iterated until the two or more design goals are met.

Figure 8:
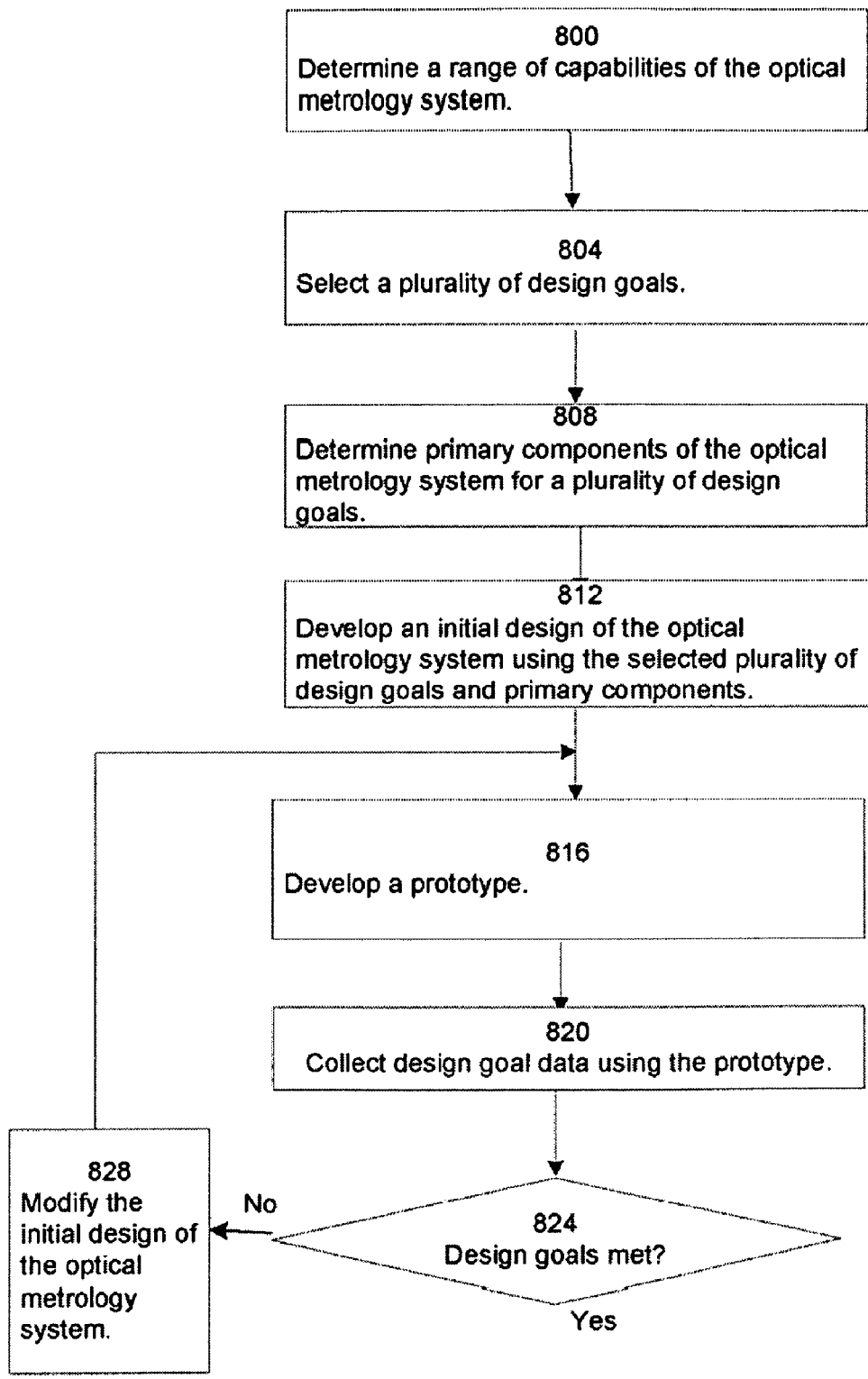
FIG. 8 depicts an exemplary flowchart for optimizing the design of an optical metrology system using primary components and a selected plurality of design goals.

FIG. 8 depicts an exemplary flowchart for optimizing the design of an optical metrology system using primary components and a selected plurality of design goals. In step 800, a range of capabilities of the optical metrology system is determined. As mentioned above, the range of capabilities includes types of applications measured and may include one dimensional repeating structures, two dimensional repeating structures, and complex structures such double patterning structures, multiple pitch structures or iso-dense structures. In step 804, a plurality of design goals is selected. In step 808, the primary components of the optical metrology system for the selected plurality of design goals are determined. Primary components are those devices or optical components that have significant impacts on a design goal. Assume the plurality of design goals include throughput, accuracy of measurement, repeatability, and measurement spot size. For the throughput design goal, the speed of the motion control system in loading and unloading a wafer has a significant impact on throughput. Similarly, the light intensity output of the bulb and consistency of the output intensity of a xenon light source have significant impact to the accuracy and repeatability of the measurements. The numerical aperture of a lens and the size of the light source bulbs impact the spot size that can be measured by the optical metrology system. For each design goal in the plurality of selected design goals, the primary components are determined either empirically or obtained based on knowledge from previous optical metrology systems or from industry and/or academic resources. Alternatively, the primary components associated with a design goal may be determined using the optimization method described in connection with FIG. 4 selecting only one design goal.

In yet another embodiment, multivariate analysis may be used to determine the correlations of primary components to a design goal of the selected plurality of design goals. For example, assume one design goal is accuracy of the measurement of the diffraction signal. Accuracy is a function of multiple variables including the intensity and temperature stability of the light sources, the intensity of the illumination and detection beams, the signal to noise ratio at various points on the optical paths, presence of a beam homogenizer, vibrations in the motion control system, residual polarization or leakage and the like. Based on comparisons of the measured diffraction signal and the simulated diffraction signal for a known structure and floating values of the variables, the variables can be correlated as to effect on the design goal of accuracy. Formalized multivariate analysis techniques can be used such as linear analysis or nonlinear analysis. Additionally, multivariate analysis can include Principal Components Analysis (PCA), Independent Component Analysis, Cross Correlation Analysis, Linear Approximation Analysis, and the like. In the example above, the intensity and temperature stability of the light sources, the intensity of the illumination and detection beams, the signal to noise ratio at various points on the optical paths, presence of a beam homogenizer, vibrations in the motion control system, residual polarization or leakage may be selected as the principal components affecting the accuracy design goal using PCA. For a detailed description of a method of applying multivariate analysis to determine the primary components or variables affecting optical metrology, refer to U.S. patent application Ser. No. 11/349,773entitled "TRANSFORMING METROLOGY DATA FROM A SEMICONDUCTOR TREATMENT SYSTEM USING MULTIVARIATE ANALYSIS", by Vuong, et al., filed on May 8, 2006, and is incorporated herein in its entirety.

In step 812, the initial design of the optical metrology system is developed based on the determined range of capabilities, the selected plurality of design goals, and primary components determined for the selected plurality of design goals. If the range of capabilities include measurement of one and two dimensional repeating structures and the design goals include throughput, accuracy of measurement, and a range of spot sizes to be measured, then the primary components determined empirically or obtained from experience or from industry and industry resources or determined using multivariate analysis will be used to develop the initial design of the optical metrology system. For example, as stated above, a motion control system for loading and aligning the wafer with the appropriate specifications, a dual light source comprising a xenon and a deuterium light sources, specific intensity bulbs for the xenon and deuterium light sources, specific beam homogenizers, specific polarizers, focusing mirrors, and use of an optical path purged with nitrogen may be utilized in the initial design.

Still referring to FIG. 8, step 816, a prototype of the optical metrology system is developed based on the initial design and selected plurality of design goals. As mentioned above, the prototype comprises two or more metrology components coupled to simulate the optical, electrical, and mechanical connections in a complete optical metrology tool. In other embodiments, the prototype is a manufactured optical metrology tool such as a reflectometer, ellipsometer, and the like. In still another embodiment, the prototype is a completely manufactured optical metrology system. In step 820, design goal data is collected using the prototype. The collected design goal data is compared to the corresponding selected plurality of design goals in step 824. If the plurality of the design goals are not met, the initial design of the optical metrology system is modified, in step 828, and the development of a prototype, collection of design goal data, comparison of the new collected design goal data, and modification of initial design of the optical metrology system, steps 816, 820, 824, and 828, are iterated until the selected plurality of design goals are met. Modifications to the initial design performed in step 828 are similar to those mentioned above in connection with step 8 of FIG. 4.

Figure 9:
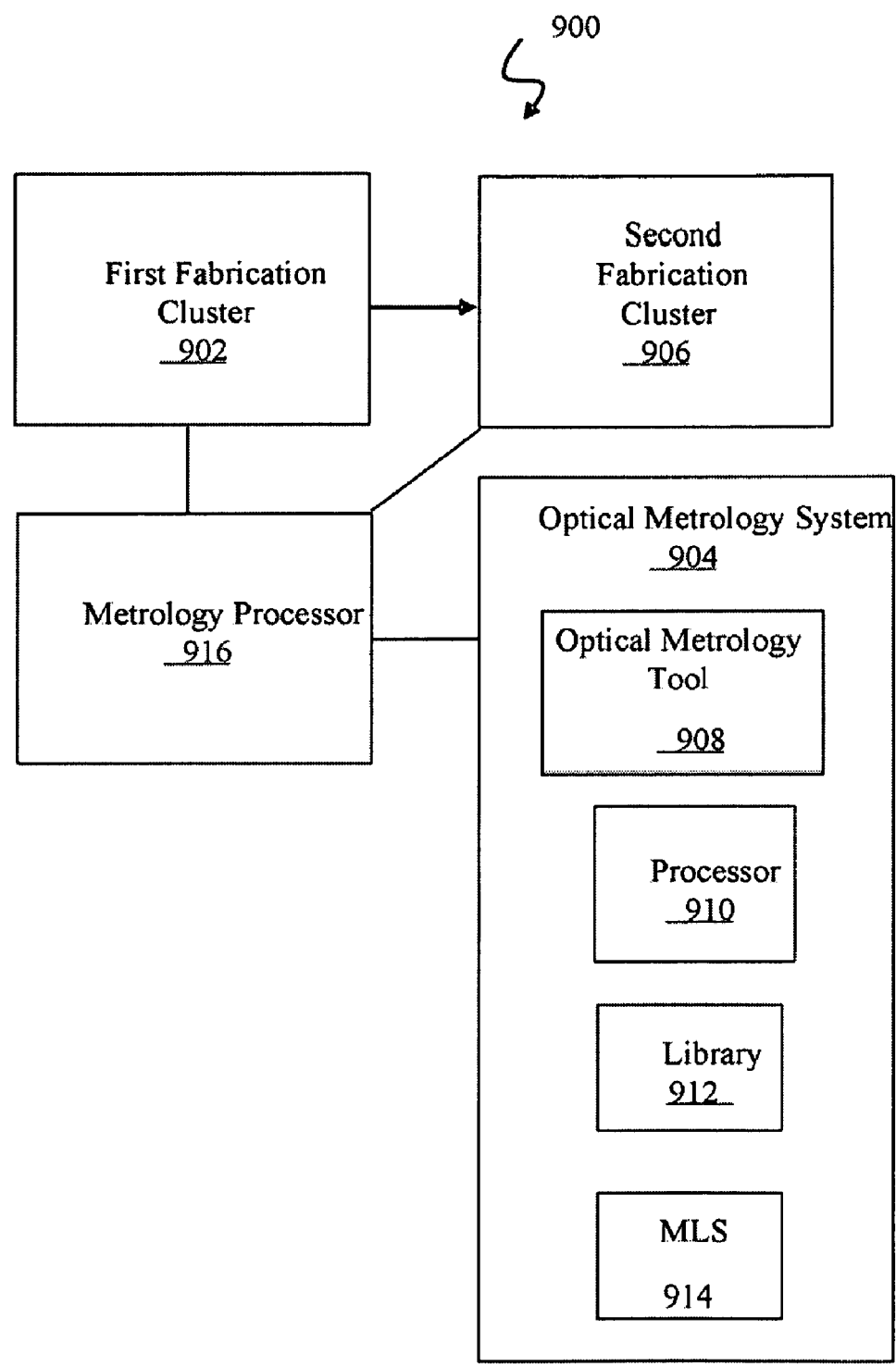
FIG. 9 is an exemplary block diagram of a system for determining and utilizing profile parameters for automated process and equipment control where the optical metrology tool was optimized with a selected plurality of design goals.

FIG. 9 is an exemplary block diagram of a system for determining and utilizing profile parameters for automated process and equipment control where the design of the optical metrology tool was optimized using a selected plurality of design goals. System 900 includes a first fabrication cluster 902 and optical metrology system 904. System 900 also includes a second fabrication cluster 906. Although the second fabrication cluster 906 is depicted in FIG. 9 as being subsequent to first fabrication cluster 902, it should be recognized that second fabrication cluster 906 can be located prior to first fabrication cluster 902 in system 900 (e.g. and in the manufacturing process flow).

A photolithographic process, such as exposing and/or developing a photoresist layer applied to a wafer, can be performed using first fabrication cluster 902. Optical metrology system 904 is similar to optical metrology system 40 of FIG. 1A. In one exemplary embodiment, optical metrology system 904 includes an optical metrology tool 908 and processor 910. Optical metrology tool 908 is configured to measure a diffraction signal off of the structure. Processor 910 is configured to compare the measured diffraction signal measured by the optical metrology tool designed to meet plurality of design goals to a simulated diffraction signal. As mentioned above, the simulated diffraction is determined using a set of profile parameters of the structure and numerical analysis based on the Maxwell equations of electromagnetic diffraction. In one exemplary embodiment, optical metrology system 904 can also include a library 912 with a plurality of simulated diffraction signals and a plurality of values of one or more profile parameters associated with the plurality of simulated diffraction signals. As described above, the library can be generated in advance; metrology processor 910 can compare a measured diffraction signal off a structure to the plurality of simulated diffraction signals in the library. When a matching simulated diffraction signal is found, the one or more values of the profile parameters associated with the matching simulated diffraction signal in the library is assumed to be the one or more values of the profile parameters used in the wafer application to fabricate the structure.

System 900 also includes a metrology processor 916. In one exemplary embodiment, processor 910 can transmit the one or more values of the one or more profile parameters to metrology processor 916. Metrology processor 916 can then adjust one or more process parameters or equipment settings of the first fabrication cluster 902 based on the one or more values of the one or more profile parameters determined using optical metrology system 904. Metrology processor 916 can also adjust one or more process parameters or equipment settings of the second fabrication cluster 906 based on the one or more values of the one or more profile parameters determined using optical metrology system 904. As noted above, fabrication cluster 906 can process the wafer before or after fabrication cluster 902. In another exemplary embodiment, processor 910 is configured to train machine learning system 914 using the set of measured diffraction signals as inputs to machine learning system 914 and profile parameters as the expected outputs of machine learning system 914.

Although exemplary embodiments have been described, various modifications can be made without departing from the spirit and/or scope of the present invention. For example, although throughput, spot size, accuracy, and repeatability of measurements were primarily used to describe the embodiments of the invention, other design goals may also be used. For automated process control, the fabrication clusters may be a track, etch, deposition, chemical-mechanical polishing, thermal, or cleaning fabrication cluster. Furthermore, the elements required for the design of the optical metrology system are substantially the same whether the optical metrology system is integrated in a fabrication cluster or used in a standalone metrology setup. Therefore, the present invention should not be construed as being limited to the specific forms shown in the drawings and described above.

What is claimed:

1. A method of controlling a fabrication cluster using an optical metrology system, the optical metrology system configure for measuring structures on a workpiece, the optical metrology system optimized using a plurality of design goals, the method comprising:

determining a range of capabilities of the optical metrology system;

determining primary components of the optical metrology system, the primary components having substantial impact to one or more design goals of a selected plurality of design goals;

setting the selected plurality of design goals to a corresponding value or range of values;

developing an initial design of the optical metrology system using selected primary components based on the selected plurality of design goals;

developing a prototype of the optical metrology system using the selected primary components;

collecting measured design goal data for the selected plurality of design goals using the optical metrology system prototype;

if the plurality of measured design goals derived from the collected measured design goal data do not match the set plurality of design goals, modifying the initial design of the optical metrology system; and iterating the developing the prototype of the optical metrology system, collecting measured design goal data, and performing a new comparison of new plurality of design goals to the set plurality of design goals until there is a match of the new measured design goals to the set plurality of design goals;

measuring a structure on a workpiece using the optical metrology system;

extracting one or more profile parameters of the structure;

transmitting at least one profile parameter of the structure to a fabrication cluster, the fabrication cluster having process parameters and equipment settings; and adjusting at least one process parameter and/or equipment setting of the fabrication cluster based on the at least one profile parameter of the structure.

2. The method for claim 1 wherein the workpiece is a wafer in a semiconductor application and wherein the optical metrology system comprises an optical metrology tool, the optical metrology tool including:
two or more light sources comprising bulbs and homogenizers;
two or more illumination beams and two or more detection beams;
a first polarizer and focusing optics for the illumination beams;
a second polarizer and collecting optics for the detection beams; and
two or more detectors generating two or more diffraction signals.

3. The method for claim 2 wherein a range of capabilities of the optical metrology system comprises measurement of one or more types of applications including one dimensional repeating structures, two dimensional repeating structures, and/or complex repeating structures comprising posts, contact holes, vias, islands, and concave or convex three dimensional structures, or combinations of two or more thereof.

4. The method of claim 2 wherein the range of capabilities of the optical metrology system comprises use of two or more light sources with each light source having a set of different wavelengths, configurable angle of incidence of the illumination beams, configurable numerical aperture for focusing optics, and one or more detectors per detection beam.

5. The method of claim 2 wherein the plurality of design goals include accuracy of diffraction signal measurement, repeatability of diffraction signal measurement, range of spot sizes of illumination beams that can be measured by the optical metrology system, range of sizes of measurement spots, throughput in the number of wafers measured per unit time, and types of applications measured.

6. The method of claim 2 wherein the plurality of design goals comprise tool-to-tool matching ranges for the optical metrology tool to similar tools or tool-to-tool matching ranges of the optical metrology tool to a reference tool, reliability of the optical metrology system expressed as up time or expressed as mean time between failures, time to develop libraries for extracting profile parameters, time to train machine learning systems for extracting profile parameters, and cost of ownership of the optical metrology system.

7. The method of claim 1 wherein the plurality of design goals include measurement of a spot size range of 32 by 32 micrometers or less, measurement accuracy of 98 percent or higher compared to measurements performed using an atomic force microscope or cross-section scanning electron microscope, and a throughput of 200 or more workpieces measured per hour.

8. The method of claim 1 wherein the plurality of design goals include measurement accuracy of 98 percent or higher compared to measurements performed using an atomic force microscope or cross-section scanning electron microscope, a repeatability of the measurement equal to or less than a 3-sigma of 4 nanometers, and a spot size range of 32 by 32 micrometers or less.

9. The method of claim 1 wherein determining primary components of the optical metrology system comprises:
using multivariate analysis to determine the primary components that have substantial impact to one or more of the selected plurality of design goals.

10. The method of claim 1 wherein the prototype of the optical metrology system includes a fully assembled optical metrology tool.

11. The method of claim 1 wherein modifying the initial design of the optical metrology system and wherein the plurality of design goals includes accuracy of the measured diffraction signal comprises:
changing the output intensity of the two or more light sources; and/or
changing the bulbs used in the two or more light sources; and/or
using one or more detectors for each of the two or more diffraction signals.

12. The method of claim 1 wherein modifying the initial design of the optical metrology system wherein the plurality of design goals includes repeatability of the measurement comprises:
selecting a first polarizer in an illumination path and a second polarizer in a detection path, wherein the first and second polarizers are configured to increase a signal to noise ratio of illumination and detection beams respectively.

13. The method of claim 1 wherein modifying the initial design of the optical metrology system includes:
using mirrors for focusing optics or using mirror focusing optics with different quality coatings, and/or
using a selectable angle of incidence for one or more illumination beams to optimize accuracy of diffraction measurements.

14. An optical metrology tool for measuring a structure on a workpiece, the optical metrology tool having primary components, the primary components having substantial impact to one or more of a selected plurality of design goals, the optical metrology tool comprising:
two or more light sources, each light source capable of generating a beam with a set of wavelengths, the two or more light sources generating two or more illumination beams;
focusing optical components configured to focus the two or more illumination beams to a structure on a workpiece;
an objective lens assembly configured to direct the two or more illumination beams onto a measurement spot on the structure, each illumination beam reaching the measurement spot at a different angle of incidence, wherein the angle of incidence of the each illumination beam is greater that zero and configured to reflect two or more detection beams off the structure;
detection beam focusing optical components configured to collect the two or more detection beams off the structure; and
one or more detectors for each of the two or more detection beams;
wherein design of the optical metrology toot is optimized using a selected plurality of design goals.

15. The optical metrology tool of claim 14 wherein the two or more light sources comprises a xenon light source and a deuterium light source.

16. The optical metrology tool of claim 14 wherein the two or more illumination beams are polarized by a common illumination polarizer and the two or more detection beams are polarized by a common detection polarizer.

17. The optical metrology tool of claim 14 wherein the selected plurality design goals include throughput, accuracy of diffraction signal measurements, repeatability of the diffraction signal measurements, and range of sizes of the measurement spot.

18. The optical metrology tool of claim 14 wherein the selected plurality design goals include throughput of 200 workpieces or more per hour and size of measurement spot of 32 by 32 microns or smaller.

19. The optical metrology tool of claim 14 wherein the illumination beam focusing optical components comprises reflective optics and detection beam focusing optical components comprises reflective optics.

20. A system for controlling a fabrication cluster using an optical metrology system, the optical metrology system optimized using a plurality of design goals, the system comprising:
   an optical metrology system optimized using a plurality of design goals, the optical metrology system configured to measure a structure on the workpiece, the workpiece having profile parameters and configured to determine a profile parameter using a profile extraction methodology;
   a metrology processor configured to transmit at least one profile parameter determined by the optical metrology system; and
   a first fabrication cluster having process parameters and equipment settings, the fabrication cluster configured to received the transmitted at least one profile parameter from the metrology processor and adjust at least one process parameter and/or equipment setting of the fabrication cluster based on the at least one profile parameter of the structure.

21. The system of claim 20 wherein the first fabrication cluster is a photolithography, an etch, a deposition, a cleaning, a track or a thermal fabrication cluster.

22. The system of claim 20 further comprising a second fabrication cluster having process parameters and equipment settings, the second fabrication cluster configured to received the transmitted at least one profile parameter from the metrology processor and adjust at least one process parameter and/or equipment setting of the second fabrication cluster based on the at least one profile parameter of the structure.

23. The system of claim 20 wherein the second fabrication cluster may be before or after the first fabrication cluster in the manufacturing flow.

* * * * *